(12) United States Patent
Ganton et al.

(10) Patent No.: US 10,177,401 B2
(45) Date of Patent: Jan. 8, 2019

(54) METHOD OF ESTABLISHING PHYSICAL AND ELECTRICAL CONNECTIONS BETWEEN A BATTERY AND A CIRCUIT

(71) Applicant: QUALCOMM Incorporated, San Diego, CA (US)

(72) Inventors: Robert Bruce Ganton, San Diego, CA (US); Robert Scott Ballam, Eatons Hill (AU)

(73) Assignee: QUALCOMM Incorporated, San Diego, CA (US)

( * ) Notice: Subject to any disclaimer, the term of this patent is extended or adjusted under 35 U.S.C. 154(b) by 464 days.

(21) Appl. No.: 14/549,202

(22) Filed: Nov. 20, 2014

(65) Prior Publication Data
US 2016/0149255 A1    May 26, 2016

(51) Int. Cl.
| | |
|---|---|
| *H01M 10/04* | (2006.01) |
| *H01M 2/02* | (2006.01) |
| *A61N 1/375* | (2006.01) |
| *H01M 2/30* | (2006.01) |
| *H01M 10/42* | (2006.01) |
| *H01R 4/2404* | (2018.01) |

(Continued)

(52) U.S. Cl.
CPC ........ *H01M 10/0436* (2013.01); *A61N 1/375* (2013.01); *H01M 2/0202* (2013.01); *H01M 2/1022* (2013.01); *H01M 2/30* (2013.01); *H01M 10/425* (2013.01); *H01R 4/2404* (2013.01); *A61N 1/378* (2013.01); *H01M 2220/30* (2013.01)

(58) Field of Classification Search
CPC .................. H01M 10/425; H01M 10/4257
See application file for complete search history.

(56) References Cited

U.S. PATENT DOCUMENTS

| 3,673,302 A | * | 6/1972 | Halsall | ................ H01M 2/0242 |
| | | | | 264/318 |
| 5,487,999 A | | 1/1996 | Farnworth | |

(Continued)

FOREIGN PATENT DOCUMENTS

| EP | 2254174 A1 | 11/2010 |
| JP | 2007179912 A | 7/2007 |

OTHER PUBLICATIONS

Solicore, Inc., "Solicore Extends Technology Innovation with World's First Digitally Printed Battery," Lakeland, Fla., Jun. 2013, 2 pages.

(Continued)

*Primary Examiner* — Olatunji A Godo
(74) *Attorney, Agent, or Firm* — The Marbury Law Group/Qualcomm

(57) ABSTRACT

A method of establishing a physical and electrical connection between a battery and a circuit board are described. The methods include applying a texture formed from conductive material to a portion of a battery exterior surface. The texture is a region populated by a plurality of protrusions. Protrusions may be configured to partially perforate and lodge within a contact surface secured to a circuit board. The battery with a texture surface may be pressed against the circuit board resulting in perforation of the contact surface by the region of protrusions. The methods may result in a battery and circuit board in electrical communication, and suitable for use within a variety of medical devices.

7 Claims, 4 Drawing Sheets

(51) Int. Cl.
*H01M 2/10* (2006.01)
*A61N 1/378* (2006.01)

(56) References Cited

U.S. PATENT DOCUMENTS

| | | | |
|---|---|---|---|
| 5,772,974 A | 6/1998 | Ohashi et al. | |
| 7,959,780 B2 | 6/2011 | Hawkins et al. | |
| 2009/0155632 A1* | 6/2009 | Byun | H01M 2/0426 429/7 |
| 2010/0086841 A1* | 4/2010 | Moon | H01M 10/425 429/156 |
| 2010/0159287 A1* | 6/2010 | Kwag | H01M 10/425 429/7 |
| 2011/0287644 A1 | 11/2011 | Kuwahara et al. | |
| 2012/0129017 A1 | 5/2012 | Ota | |
| 2012/0315507 A1* | 12/2012 | Kim | H01M 2/105 429/7 |
| 2014/0031890 A1 | 1/2014 | Mashiach et al. | |
| 2014/0121557 A1 | 5/2014 | Gannon et al. | |

OTHER PUBLICATIONS

International Search Report and Written Opinion—PCT/US2015/057343—ISA/EPO—dated Feb. 8, 2016.

* cited by examiner

METHOD OF ESTABLISHING PHYSICAL AND ELECTRICAL CONNECTIONS BETWEEN A BATTERY AND A CIRCUIT

BACKGROUND

It is increasingly common for medical devices to be electronic providing functionality from electrical circuits powered by onboard batteries. Additional components such as sensors, piezo-electric elements, transceivers, and storage media may also be integrated into the medical device. Proper function of electrical medical devices requires that all components and assembly materials are suitable for extended use on or within a human body, and thus will not corrode or introduce toxic elements to the patient. Costs associated with manufacturing implant grade circuits and electrical components may be high and the manufacturing process time consuming.

SUMMARY

The various embodiments provide improved methods, surface treatments and batteries for coupling a battery or other electrical power source to a circuit. In an embodiment, a battery may include a textured conductive surface, such as one or more battery terminals, that is configured to provide an electrical connection to a contact. In an embodiment, the textured surface may include a region of protrusions, which may be pointed, barbed, conical, etc. In some embodiments, the protrusions may be configured to partially penetrate a contact surface providing a physical connection in addition to an electrical connection. In some embodiments, the textured surface may be integral to the battery casing. Other embodiments, the battery may include a textured surface that is affixed to a conductive surface of the battery casing, such as textured conductive layer applied to one or more terminals of the battery.

The various embodiments may be used to electrically and physically connect a battery to a medical device having a circuit board. During assembly of such a medical device, the textured surface of the battery may be pressed onto the conductive surfaces of the medical device until the textured surface engages the contact layer to form a physical and electrical connection.

An embodiment includes a method for establishing a physical and electrical connection between a battery and a circuit. The embodiment method may include forming a textured surface on a conductive portion of a battery exterior, and pressing the textured surface of the battery onto a contact surface of a circuit. Textured surfaces applied to or formed on a battery may include a region of raised protrusions, such as spikes, barbs, nubs, or conical shapes, that may be configured to partially penetrate one or more layers of a contact. For example, the one or more contact layers may include a copper layer covered by a gold layer that is covered a protective polymer layer, and the protrusions may be configured to penetrate the protective polymer layer and engage (or partially penetrate) the gold layer. In an embodiment the method may further include applying an adhesive to one or both of the battery textured surface and the contact surface prior to pressing the textured surface onto the contact surface.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

Figure 1:
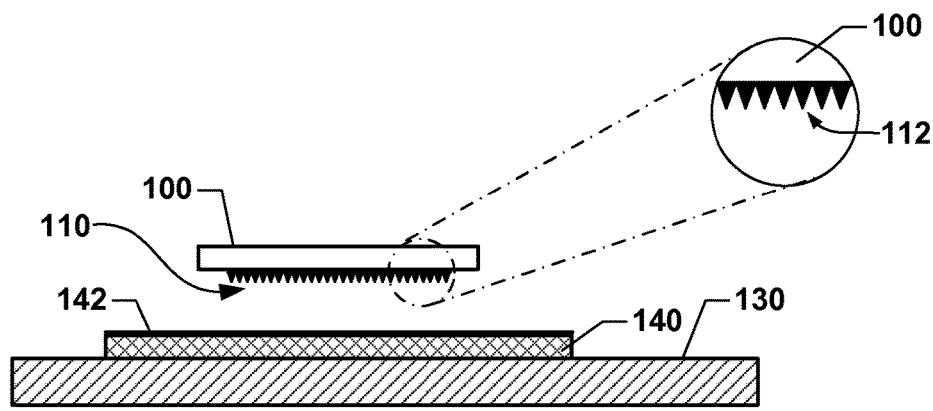
FIG. 1 is a side view of an IC module being connected to a battery having texturization in accordance with various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The term "medical device" is used herein to refer to any electronic device that may be applied to or implanted within a patient and configured to perform any of a variety of medical functions. The various embodiment components, surface treatments and methods are described using medical devices as an example implementation; however, the various embodiments may be used with any circuit requiring a securely attached battery or electrical power source.

The words "first," "second," "third," and similar terms are used herein for clarity purposes to distinguish various described elements and are not intended to limit the claims to a particular order or hierarchy of elements.

Various embodiments include a battery that may have a textured surface along at least a portion of the battery exterior. The textured surface may be designed to engage (e.g., secured to) a contact surface of a circuit board. Pressure applied to the battery in the direction of a connection or contact of a circuit board may result in electrical and physical engagement of the battery to the contact surface of the circuit board.

Various embodiments include surface treatments for batteries and a method of establishing a secure connection between a battery and a circuit element. The method is well suited to use in the assembly of medical devices because the method negates the need for bonding agents that could be harmful to the human anatomy. The method may include applying a texture to a battery surface. Applying texture to the battery surface may include the creation of a region populated with protrusions. Such protrusions may include spikes, needles, spines, cones, pyramids, barbs or the like, and may depend upon a chosen method of construction.

The textured region of the battery may be pressed onto a contact surface of a circuit element. Pressure may be exerted until the protrusions engage or make an electrical connection with a contact surface affixed to a circuit board. In some embodiments, the protrusions may deform during application of pressure, resulting in the flattening or splaying of end portions of the protrusions, which may serve to provide physical connection to the contact surface. A physical connection may be maintained as a result of protrusion deformation that renders individual protrusions unable to retreat through the perforation holes. In this way, batteries may be electrically and physically connected to a contact surface of an electrical device. The engaging of the contact surface by the protrusions on the battery surface may improve an electrical connection between the battery and the contact, thereby enabling the flow of current between a battery terminal and the contact.

A protective layer may be applied to the exterior of the contact surface, which may reduce or prevent oxidization of the contact surface, and the protrusions disposed on a battery surface may be designed to penetrate the protective layer so as to electrically engage the underlying contact surface. In this manner, the region of protrusions may make a physical and electrical connection with the contact surface even when a protective layer is applied to the contact surface.

Adding a textured surface to a battery and the embodiment method may be well suited for use in assembly of medical devices. A battery having a textured surface for engaging a contact surface may be pressed into connection with a circuit board at any time in the assembly process. Connection may be made in a factory, where a roller may exert pressure on the battery and circuit. Alternatively, the battery may be manually pressed to a circuit by a technician at a time prior to use of the medical device.

FIG. 1 illustrates a side cross-sectional view of an exemplary battery 100 during a stage of the embodiment method. The battery 100 may have a textured surface 110 featuring a region of protrusions 112 extending away from the battery 100 surface. Such protrusions 112 may be configured to engage a contact surface 140 secured to a side of a circuit board 130, with application of pressure. The exertion of force on a side of the battery 100 opposing the textured surface 110, towards a contact surface 140 can result in connection of the battery 100 to the circuit board 130. Because the textured surface is composed of conductive material, the engagement can place the battery 100 and circuit board 130 in electrical communication via the physical and electrical connection of the textured surface 110 to the contact surface 140. The connection enables charge to flow from the battery 100 terminal(s), through the textured surface 110 and the protrusions 112, into the contact surface 140, and to the circuit board 130.

In various embodiments, a protective layer 142 may wholly or partially cover the contact surface 140. Such a protective layer 142 may reduce or prevent oxidization of the contact surface 140 by limiting exposure of the contact surface 140 to the surrounding environment. The textured surface 110 may be designed to perforate the protective layer 142 so as to engage the underlying contact surface 140. The protective layer 142 may be a film, polymer coating, polymer, film, adhesive coating, adhesive film, etc.

Figure 3:
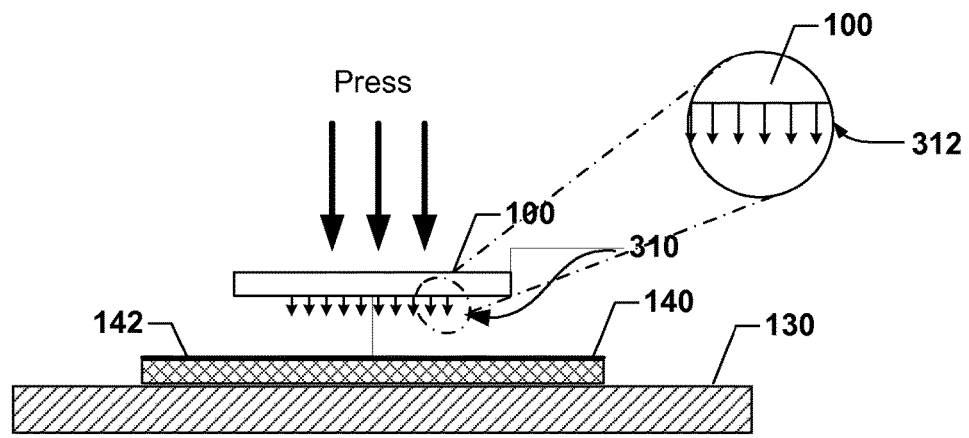
FIG. 3 is a side view of an IC module being connected to a battery having alternate texturization in accordance with various embodiments.

The battery 100 may have a textured surface 110 on a portion of the battery 100 exterior, as illustrated in FIGS. 1 and 3. In some embodiments, the textured surface 110 may be formed directly on the surface of the battery 100, such as in material deposition methods. In some embodiments, the textured surface 110 may be formed integral to the battery casing. In some embodiments, a separate, pre-formed textured surface 110 may be affixed to an exterior of the battery 100. The battery 100 may be easily affixed in physical and electrical connection with a contact surface 140 of a circuit board 130 via the embodiment method described herein. Such a battery 100 may be advantageous for use with medical devices, because there may be no need for the use of potentially harmful bonding agents.

Figure 2:
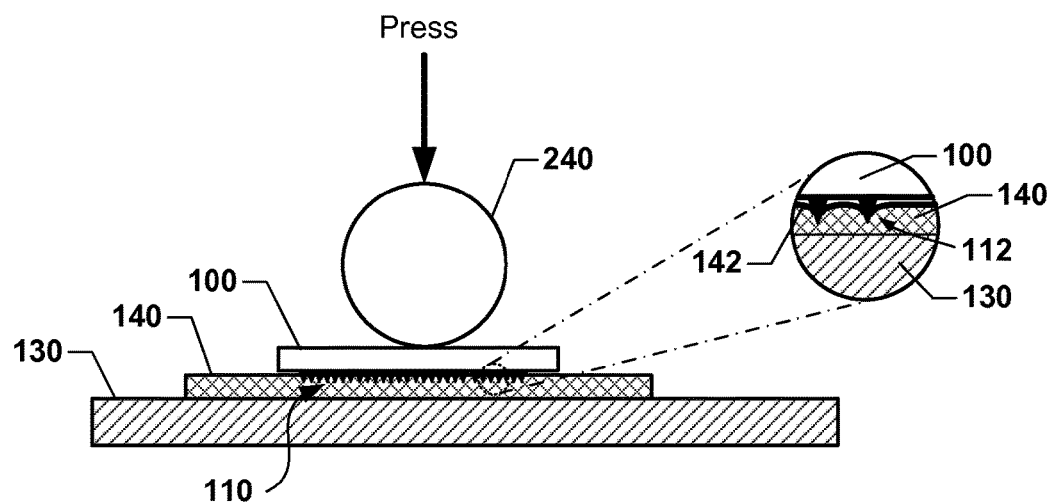
FIG. 2 is a side view of the IC module of FIG. 1 secured to a battery in accordance with various embodiments.

FIG. 2 illustrates the battery 100 of FIG. 1 in a final stage of the process, secured to a contact surface 140 of a circuit board 130. The textured surface 110 in the form of a region of protrusions 112 extending from a battery 100 surface engages via partial perforation, a contact surface 140 secured to the circuit board 130. In some embodiments, a roller 240 may be used to exert force on the battery 100, thereby pressing the textured surface 110 into the contact surface 140. As the textured surface 110 region of protrusions 112 penetrates the contact surface 140, the protrusions 112 may deform such as by bending, twisting, flattening, or the like. Each protrusion 112 may be trapped within the contact surface 140, unable to retreat through the entry aperture, because the deformed shape or orientation may be different from that of the pre-insertion protrusion 112.

The bond between the textured surface 110 and contact surface 140 may be improved using various techniques. For example, electrostatic force may further aid in maintaining connection of the textured surface 110 to the contact surface 140. As another example, adhesive may optionally be applied during connection of the battery 100 to the circuit board 130 to improve the bond between the textured surface 110 and the contact surface 140. As yet another example, current flowing through the textured surface 110 into the contact surface 140 during manufacture or use of the battery, may create an alloy zone that may aid in bonding the surfaces together. As a further example, heating the textured surface 110 and/or contact surface 140 during engagement may also strengthen the bond therebetween. In some embodiments, the protrusions 112 may have a height less than the thickness of the target contact surface 140. By way of example, a target contact surface 140 having a thickness of seven thousandths of an inch may warrant protrusions having a height of seventy to one hundred microns. The radius of protrusions may be half a millimeter to a quarter millimeter. In various embodiments, including multiple contact surfaces 140 in a stacked configuration may enable use of protrusions 112 of greater height or diameter due to the capacity for deeper protrusion 112 penetration. In some embodiments, such as those employing flexible electronics or flex circuits, the protrusions 112 may have a height greater than, equal to, or less than the contact surface 140, allowing the protrusions 112 to fully penetrate the contact surface and extend into the circuit 130. The region of protrusions 112 may be constructed of a material stronger than that of the contact surface 140 to ensure that protrusion deformation does not occur prior to partial perforation. In the illustrated example, each protrusion 112 has a spiked or conical shape that enables easy piercing of the contact surface 140 and is prone to deformation upon insertion into the one or more contact surfaces 140. Although protrusions 112 are shown to have spiked or conical shapes, persons skilled in the art will appreciate that protrusions 112 may have any suitable shape.

In some electronic devices, the contact surface 140 may have only a single conductive material layer of (e.g., copper or gold), with an optional protective layer. In some embodiments, a protective layer 142 may be disposed on top of the contact surface 140. For example, the single contact surface 140 may be a copper layer and the protective layer 142 may be a polymer layer to prevent oxidization. Alternatively, a gold leaf layer with an optional protective layer may be used as the single contact surface 140.

In some embodiments, the contact surface 140 may be made up of multiple layers of materials, such as a gold conductive layer applied over a copper conductive layer. The inclusion of a gold layer may be desirous in embodiments in which no adhesive is applied during the engagement process, because gold is easily deformed by protrusions on the battery surface. This allows gold atoms to flow around the protrusions, and consequently a strong bond can be created between the textured surface 110 and contact surface(s) 140. In such embodiments, a similar polymer protective layer 142 may be disposed on top of the multi-layered contact surface 140.

FIG. 3 illustrates an alternative configuration of the textured surface 310 having a region of protrusions 312 that include a barb-like shape. Like the region of protrusions 112 shown in FIG. 1, the barbed protrusions may be designed to engage a contact surface 140 secured to a circuit board 130.

Figure 4:
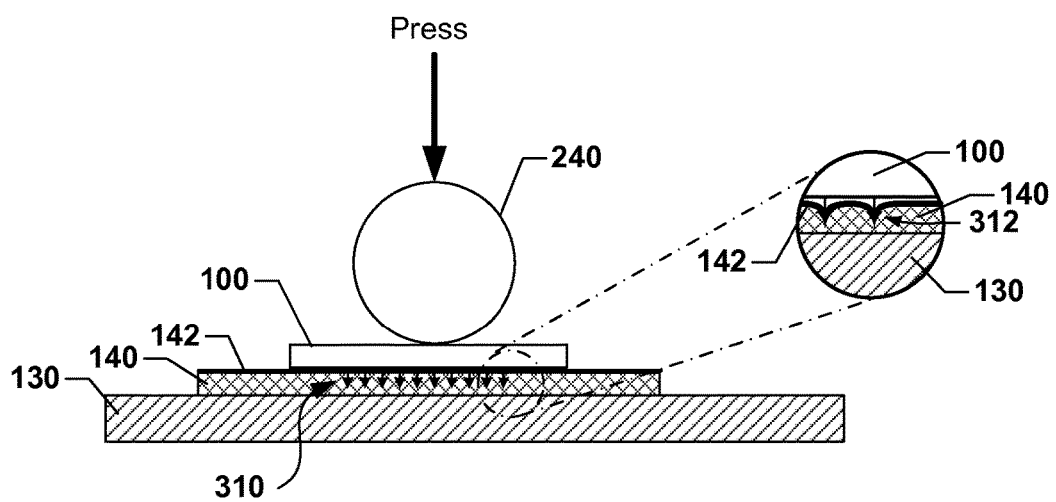
FIG. 4 is a side view of the IC module of FIG. 3 secured to a battery in accordance with various embodiments.

FIG. 4 illustrates the connection of an alternative configuration of the textured surface 310 to the contact surface 140. The engagement of the textured surface 310 to the contact surface 140 may physically and electrically connect the battery 100 to a circuit board 130. The individual protrusions 312 have a barbed shape configured to lodge in the contact surface 140 when the battery 100 is pressed against the contact surface 140. The increased surface-to-surface contact provided by the barbed shape of the protrusions 312 may result in a stronger physical connection to the contact surface 140 and lower electrical resistance between the battery 100 and the contact.

The bond between the textured surface 110 and contact surface 140 may be improved using various techniques. For example, current flowing through the textured surface 110 barbs into the contact surface 140 may create an alloy zone that aids in bonding. As another example, heating the textured surface 110 and/or contact surface 140 during engagement may strengthen the bond therebetween.

The relative size and shape of the battery 100, textured surface 110 and region of protrusions 112, contact surface 140, and circuit board 130 in the drawings are intended for illustrative purposes only. The size and shape of any of these elements may be modified to suit a particular or a general purpose. In particular, the region of protrusions 112 may be much thinner in width in order to engage the contact surface 140 with little resistance, and may be longer or shorter depending upon the depth of penetration appropriate for the particular contact surface(s) 140. Similarly, the configuration of individual components is for illustrative purposes only, and the size and location of components will depend on the particular design.

Figure 5:
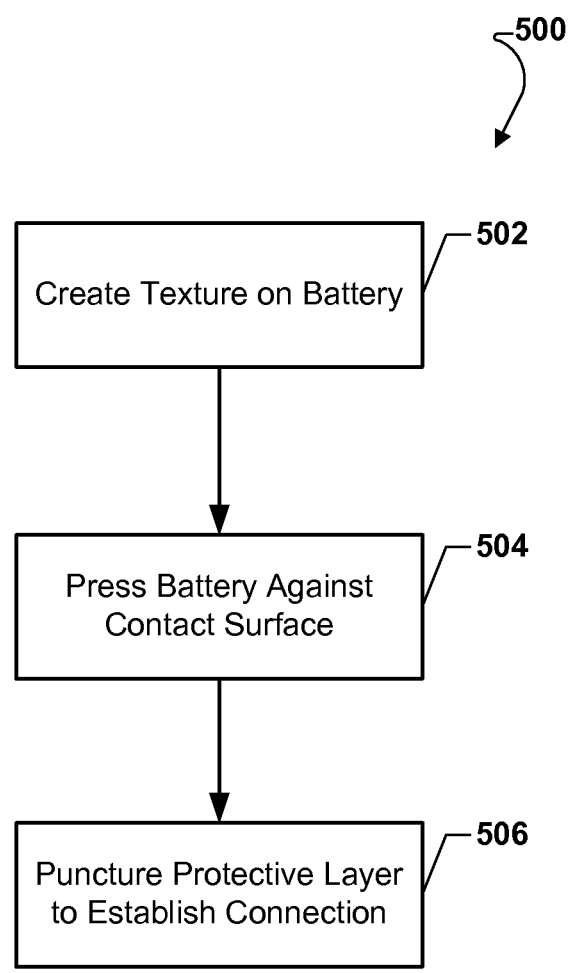
FIG. 5 is a flow process diagram illustrating a method of establishing a physical and electrical connection between a battery and an IC module in accordance with various embodiments.

FIG. 5 illustrates an embodiment method 500 of establishing physical and electrical connection between the battery and circuit board of FIGS. 1-4, in accordance with various embodiments.

In block 502, a texture may be created on or applied to a battery. The textured surface may be a region of raised protrusions suitable for engaging, such as by piercing or partially perforating a contact surface. Such protrusions may be spikes, cones, needles, pyramids, barbs or the like. By way of example, electric region vapor deposition techniques may be used to build the textured surface on a battery exterior. Alternatively, stamped nickel strips may be welded to a surface of the battery at the time of assembly. In some embodiments, a texture may be molded integral to the battery casing. The precise technique used to create or apply the textured surface to the battery is not limited to any particular method, and the techniques described herein are for exemplary purposes only.

Any positioning and pattern of textured surface may be employed. Shape and size of textured surface elements may also vary according to the composition and thickness of the target contact surface. By way of example, a single copper or gold contact surface with a protective polymer layer may tolerate protrusions of 70 microns in height and a quarter millimeter diameter, while a multi-layered contact surface of copper and gold with a polymer film may tolerate individual protrusion size of about 100 microns in height and a half millimeter in diameter.

A variety of methods may be employed in the creation of the textured surface. For purposes of illustration, electric vapor deposition, electro-chemical processes, micro-welding, other forms of material deposition and 3-D printing are among the possible methods for applying texture to the battery surface. In an alternative embodiment, texture may be formed in the battery surface through machining or deformation of the battery contact and/or case material, such as through molding, machining, stamping or milling. Such machining or deformation may be accomplished on the battery contact surface before or after the battery is assembled. In a further embodiment, texture may be formed in a conductive material separate from the battery, such as by molding, machining, stamping or milling a textured surface on or from a nickel strip that is attached to the battery via spot welding or similar technique. In still another embodiment, the battery housing may be formed with the texture integrated onto terminals prior to battery assembly, such as by metal stamping of the housing. The selection of a texturization process and a conductive material for textured surface construction may be determined by the practitioner.

In block 504, pressure may be applied to the battery to press it onto a contact surface in order to facilitate engagement with the contact surface. Orientation of battery may be changed to align the textured surface in parallel with the circuit board contact surface. Force may be applied to a portion of the battery opposing the textured surface in the direction of the contact surface, thereby pressing the textured surface into the contact surface and engaging the two. In various embodiments, the battery may be installed in a factory and machinery such as a roller, may be used to press the battery's textured surface onto the circuit board contact surface. In some embodiments, the battery may be installed just prior to use of a host device, and may be manually pressed into the circuit board contact surface by a technician.

In block 506, a protective layer, if present, is punctured by the battery textured surface to establish a connection. The battery textured surface is designed to push through the protective layer and electrically engage, and optionally to partially perforate, the contact surface. The protrusions may have sufficient rigidity and size to enter and lodge in the contact surface media. Engaging the textured surface with the contact surface results in the electrical and physical connection between the battery and the contact surface of the circuit board. As discussed above, the textured surface may partially deform into the contact surface as a result of the contact pressure, which may function to form a physical bond for holding the battery to the contact surface. In some embodiments, the connection of the textured surface to the contact surface may be maintained by the shape of the protrusions, such as via barbs as illustrated in FIGS. 3-4. In this manner, a battery may be easily and inexpensively secured to a circuit board.

Figure 6:
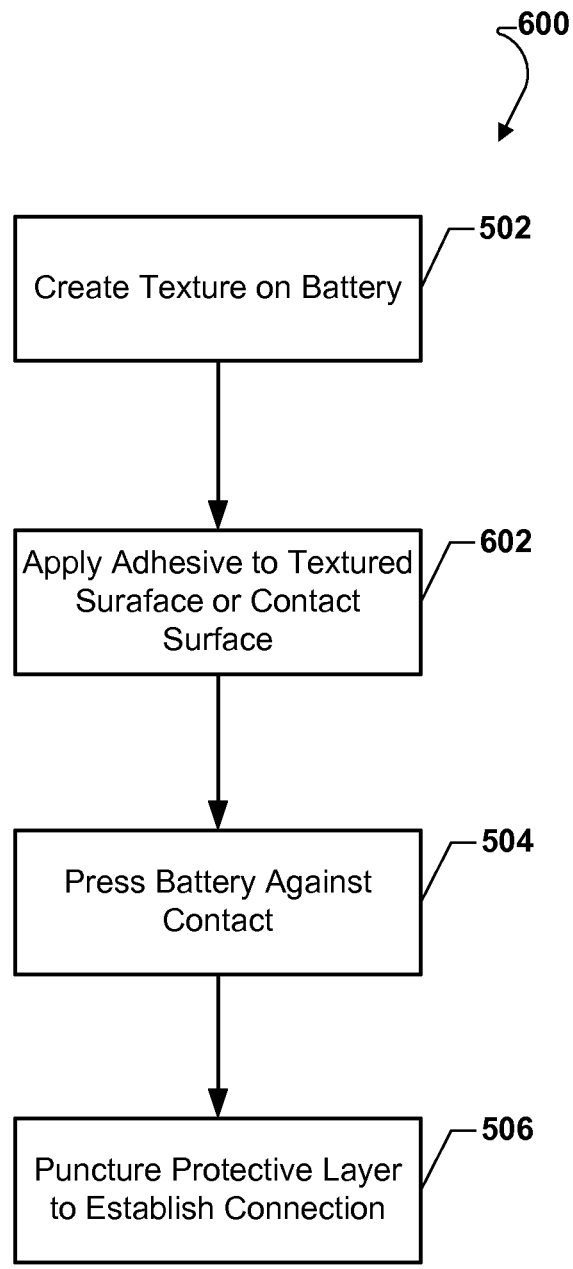
FIG. 6 is a flow process diagram illustrating a method of establishing a physical and electrical connection between a battery and an IC module in accordance with various embodiments.

FIG. 6 illustrates another embodiment method 600 of establishing physical and electrical connection between the battery and circuit board of FIGS. 1-4, in accordance with various embodiments.

In block 502, a textured surface may be created on or applied to a portion of the surface of a battery. This operation may be carried out in the manner described above with reference to FIG. 5.

In block 602, an adhesive may be applied to the textured surface or the contact surface. In various embodiments, assembly may occur in a factory and time may be allotted for an adhesive to set. Conductive epoxies may be used in lengthy assembly configurations, as they are well suited to securing the textured surface to the contact surface but may require significant setting periods. In various embodiments, where assembly time allocations are short, an adhesive film placed between the textured surface and contact surface may used to improve engagement of the textured surface to the contact surface. Adhesives may shrink as they dry, pulling the textured surface closer to the contact surface and improving bonding. Like all components of the assembly, the adhesive may be safe for application onto or insertion into a human body, and may be disposable.

The various embodiments improve the use of an adhesive in block 602 because the surface roughness and/or protrusions from the battery surface can press through the adhesive to directly contact and, in some cases, partially penetrate the contact surface to create an electrical connection. Thus, the surface protrusions may enable a low-resistance electrical connection to a contact surface even when there is a layer of adhesive between the battery and the contact surface. Following application of the adhesive in block 602, remaining operations in blocks 504 and 506 may be carried out as described in FIG. 5.

Any reference to claim elements in the singular, for example, using the articles "a," "an" or "the" is not to be construed as limiting the element to the singular.

One skilled in the relevant art will recognize that many possible modifications and combinations of the aspects of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the disclosure to the precise forms disclosed. Many modifications and variations are possible in view of the above teachings. The embodiments were chosen and described to explain the principles of the disclosure and their practical applications, and to enable others skilled in the art to best utilize the disclosure and various embodiments with various modifications as suited to the particular use contemplated. Thus, the present disclosure is not intended to be limited to the embodiments and individual aspects of the disclosed technologies shown and described herein, but is to be accorded the widest scope consistent with the following claims and the principles and novel features disclosed herein.

What is claimed is:

1. A battery, comprising:
   a textured surface including a region of raised protrusions, the raised protrusions on an electrically conductive portion of an exterior of the battery, wherein the textured surface is configured to at least partially perforate a contact surface of a circuit board and engage in a physical and electrical connection with the contact surface of the circuit board.

2. The battery of claim 1, wherein the raised protrusions have a spike shape.

3. The battery of claim 1, wherein the raised protrusions have a barbed or conical shape.

4. The battery of claim 1, wherein the textured surface is disposed on a battery terminal.

5. The battery of claim 1, wherein the textured surface is integral to a battery casing.

6. The battery of claim 1, wherein the textured surface is directly affixed to the battery.

7. The battery of claim 1, wherein the textured surface is secured to a portion of the exterior of the battery.

* * * * *